United States Patent
Gavezotti et al.

[19]

[11] Patent Number: 6,166,252

[45] Date of Patent: Dec. 26, 2000

[54] PROCESS FOR PREPARING DICHLOROFLUOROACETYL HALIDES

[75] Inventors: Piero Gavezotti, Milan; Julio A. Abusleme, Saronn; Vito Tortelli, Milan, all of Italy

[73] Assignee: Ausimont S.p.A., Milan, Italy

[21] Appl. No.: 09/226,121

[22] Filed: Jan. 7, 1999

[30] Foreign Application Priority Data

Jan. 9, 1998 [IT] Italy .................................. MI98A0013

[51] Int. Cl.⁷ .......................... C07C 51/58; C07C 53/21
[52] U.S. Cl. ........................... 562/852; 562/862; 562/605
[58] Field of Search .............................................. 562/852

[56] References Cited

U.S. PATENT DOCUMENTS

| | | |
|---|---|---|
| 3,287,424 | 11/1966 | Pacini et al. . |
| 3,624,250 | 11/1971 | Carlson . |
| 3,859,424 | 1/1975 | Scherer et al. . |
| 4,524,194 | 6/1985 | Dumoulin . |
| 5,569,728 | 10/1996 | Abusleme et al. . |

FOREIGN PATENT DOCUMENTS

| | | |
|---|---|---|
| 0 185 242 A2 | 6/1986 | European Pat. Off. . |
| 0 526 216 A2 | 2/1993 | European Pat. Off. . |
| 0 691 322 | 1/1996 | European Pat. Off. . |
| 976 316 | 11/1964 | United Kingdom . |
| 976316 | 11/1964 | United Kingdom . |

OTHER PUBLICATIONS

J. Org. Chem. 47, (1982) pp. 2009–2013, "Thermal Decomposition of Some Perfluoro–and Polyfluorodiacyl Peroxides" Chengxue et al.,.

*Primary Examiner*—Paul J. Killos
*Attorney, Agent, or Firm*—Arent, Fox, Kintner, Plotkin & Kahn

[57] ABSTRACT

Process for preparing dichlorofluoroacetylfluoride ($CFCl_2COF$) comprising the following steps:

a) fluorination with hydrofluoric acid (HF) of the trichloroacetyl halide in a fixed or fluidized tubular bed reactor, filled with fluorination catalysts and having a temperature profile between the inlet of the reactants and the outlet of the reaction products, in the range from 175° C. to 275° C.

b) distillation of the reaction products with trichloroacetylfluoride recycle and recovery of a mixture formed by HF and $CFCl_2COF$;

c) separation of the HF/$CFCl_2COF$ mixture components by cooling at temperatures lower than −10° C., and optionally the HF recycle.

11 Claims, No Drawings

PROCESS FOR PREPARING DICHLOROFLUOROACETYL HALIDES

The present invention relates to a process for preparing dichlorofluoroacetyl halides, more specifically dichlorofluoroacetylfluoride.

Various kinds of containing hydrogen fluorinated polymers having thermoplastic properties are known in the art. A first class is per (halo) fluoroolefin copolymers with non halogenated olefins, such as for example tetrafluoroethylene (TFE) or chlorotrifluoroethylene (CTFE) copolymers with ethylene (ETFE, ECTFE), optionally containing a third fluorinated comonomer in amount in the range 0.1–10% by moles (see for instance U.S. Pat. No. 3,624,250). The said copolymer preparation is generally carried out in suspension and, especially in the case of CTFE/ethylene copolymers, is preferably carried out at low temperature (lower than 30° C.). A low polymerization temperature is absolutely necessary to favour the alternation among the comonomers, avoiding the ethylene block formation, which would cause worsening of the mechanical properties and would render the polymer thermally unstable.

Another class of thermoplastic fluoropolymers containing hydrogen is polyvinylidenfluoride (PVDF) and modified PVDF with small amounts (0.1–10% by moles) of other fluorinated comonomers. Said products can be prepared by suspension (co)polymerization, as described for example in EP 526,216, preferably in the presence of a suitable suspending agent, for instance polyvinylalcohol or cellulose hydrosoluble derivatives, as described in U.S. Pat. No. 4,524,194. Depending on the type of the used initiator, it is possible to operate at different temperature ranges, also below 3°0 C. The fact to operate at low temperatures allows to obtain an improved structural order, in particular a monomeric inversion decrease, and consequently a higher cristallinity percentage, from which, as it is known, a second melting temperature and, therefore, a higher working maximum temperature derives. However the fact to operate at low temperatures does not guarantee a priori a high thermal stability, since it depends also on the chain end group nature deriving from the polymerization initiator. It is indeed known that said end groups can be unstable and that their decomposition can give rise to dehydrohalogenation reactions along the polymeric chain, with hydrohalogenic acid development and formation of double bonds, which give the product undesired colorations (the so called discoloration phenomenon).

Due to the low reaction temperature, the radical initiators employable in such processes can be selected inside a rather restricted class. The most commonly used are the bis-acylperoxides having the formula $(R_f-CO-O)_2$, wherein $R_f$ is a $C_1-C_{10}$(per)haloalkyl (see for example EP 185,242 and U.S. Pat. No. 3,624,250). Among them, bis-dichlorofluoroacetylperoxide (DCFAP) is particularly preferred; it gives to the hydrogen containing polymers (for example ETFE, ECTFE, PVDF) a higher thermal stability in comparison with tri-chloroacetylperoxide (TCAP). (See the U.S. Pat. No. 5,569,728). The DCFAP has indeed a thermal half time clearly lower than bis-trifluoroacetylperoxide and bis-difluorochloroacetylperoxide and therefore the polymerization, in the presence or in absence of water, which uses DCFAP, at low temperature, takes place with kinetics compatible with the industrial processes. Moreover the bis-trifluoroacetylperoxide and bis-difluorochloroacetylperoxide have a very low stability to hydrolysis and therefore their use in polymerizations in the presence of water is very problematic since high amounts of initiators are required.

It was therefore felt the need to have available an efficient process, with reactant quantitative conversion, allowing to obtain high purity dichlorofluoroacetylfluoride ($CFCl_2COF$), precursor of bis-dichlorofluoroacetylperoxide. Therefore the industrial process for the dichlorofluoroacetylfluoride preparation must not lead to the formation of meaningful amounts of by-products which substantially lower the reactant conversion into $CFCl_2COF$, requiring disposal plants.

The Applicant has surprisingly and unexpectedly found a process characterized by reactant quantitative conversion for preparing high purity dichlorofluoroacetylfluoride and wherein the undesired by-products amount, chlorodifluoroacetylfluoride and trifluoroacetylfluoride, is at very low levels such as not to require disposal plants.

It is therefore an object of the present invention a process comprising the following steps:

a) fluorination with hydrofluoric acid (HF) of the trichloroacetyl halide in a fixed or fluidized tubular bed reactor, filled with fluorination catalysts and having a temperature profile between the reactant input and the reaction product output, in the range from 175° C. to 275° C., preferably the tubular reactor temperature profile ranges from 200° C. to 260° C.;

b) distillation of the reaction products with recycle of trichloroacetylfluoride and recovery of a mixture formed by HF and $CFCL_2COF$;

c) separation of the components of the HF/$CFCl_2COF$ mixture by cooling at temperatures lower than −10° C., preferably at temperatures lower than −30° C., and optionally the HF recycle.

Step a) can be carried out in a fixed or fluidized bed reactor, as said, with fluorination catalysts at a substantially constant temperature selected in the range from 200° C. to 260° C., preferably from 220° C. to 250 ° C. various kinds of catalysts of the organic molecules fluorination, known in the art, can be used in the process object of the present invention. As an example the Cr- or Ni-based catalysts can be mentioned. More specifically catalysts comprising chromium oxide, optionally containing small amounts of iron, cobalt, aluminum, zirconium, manganese, bismuth, thorium and/or nickel oxide; catalysts comprising chromium fluoride, optionally containing small amounts of iron, cobalt, aluminum, zirconium, manganese, bismuth, thorium and/or nickel oxide, are preferred.

The chromium oxide of the catalysts can be prepared, for example, by partial or total dehydration of the chromium hydroxide gel. The anhydrous chromium oxide can be obtained by calcination of chromium inorganic salts such as ammonium chromate and chromium nitrate, or by calcination of chromium organic salts such as oxalates and chromium formates.

The above described catalysts can be also supported for example on aluminum fluoride in particular of gamma form.

The catalysts can be prepared with the sizes suitable for fixed or fluidized bed according to technologies known in the art.

The $CFCl_2COF$ product subjected to alkaline ambient oxidation gives rise to dichlorofluoroacetylperoxide, see for instance J. Org. Chem., 47, 2009–2013 (1982). If desired, $CFCl_2COF$ can be transformed into dichlorofluoroacetylchloride ($CFCl_2COCl$), which, having a higher boiling temperature, is more easily handy in the successive oxidation process to obtain DCFAP.

The $CFCl_2COF$ to $CFCl_2COCl$ reaction occurs by hydrolizing with water and then treating, at a temperature in the range −20° C.−+80° C., with thionyl chloride in a ratio of about 3/1 by moles based on the moles of the dichlorofluoroacetic acid (CFCl$_2$COOH) and in the presence of a 10% by moles of pyridine based on the CFCl$_2$COOH moles. In general the reaction yield increases with the temperature.

The invention process is surprising since by operating in the above indicated conditions it allows to obtain with quantitative conversion the CFCl$_2$COF with a 98% by weight purity, the HF being the remaining part.

An embodiment of the present invention is reported hereinafter as an example; its purpose is merely illustrative and not limitative of the scope of the invention itself.

EXAMPLE

In a tubular reactor containing 200 g of Cr$_2$O$_3$ catalyst, previously dried at 350° C. with nitrogen, a gaseous mixture of CCl$_3$COCl and HF coming from a prevaporizer in a ⅓ molar ratio is fed. The adiabatic tubular reactor is thermostated with a temperature profile ranging from 200° C. at the gaseous mixture input up to 255° C. at the gase output. The reaction products are condensed at −75° C. 495 g of CCl$_3$COCl were fed during two hours. The gaschromatographic analysis of the reaction products shows the presence of HF, HCl, CCl$_3$COF, CFCl$_2$COF and CF$_2$ClCOF. The CCl$_3$COCl conversion is quantitative. The selectivity to CFCl$_2$COF is of 50% by moles, being the reminder converted essentially CCl$_3$COF. The CFCl$_2$COF/CF$_2$ClCOF molar ratio is 94. The condensate distillation in a 30 theoric plates column leads to the separation of the HF/CFCl$_2$COF mixture from CCl$_3$COF, from CF$_2$ClCOF and from HCl. Then the dichlorofluoroacetylfluoride is purified by separating HF at −40° C. as upper phase. The CFCl$_2$COF final purity obtained by gas-chromatography was of 98% by weight.

What is claimed is:

1. A process for preparing dichlorofluoroacetylfluoride (CFCl$_2$COF) comprising the following steps:

a) fluorinating trichloroacetyl halide with hydrofluoric acid in a fixed bed or a fluidized tubular bed reactor, filled with fluorination catalysts based on chromium oxide and optionally containing small amounts of iron, cobalt, aluminum, zirconium, manganese, bismuth, thorium and/or nickel oxide, having a temperature profile between the reactant input and the reaction product output, in a range of 175° C. to 275° C.;

b) distilling the reactant products with recycle of trichloroacetyl fluoride and recovering a mixture formed by HF and CFCl$_2$COF;

c) separating the compounds of the HF/CFCl$_2$COF mixture by cooling at temperature lower than −10° C., and optionally the HF recycle.

2. Process according to claim 1 wherein in the step a) the temperature profile of the tubular reactor ranges from 200° C. to 260° C.

3. Process according to claim 1, wherein in the step c) the separation occurs at temperatures lower than −30° C.

4. Process according to claim 1, wherein the step a) is carried out in a fixed or fluidized bed reactor with fluorination catalysts at a substantially constant temperature selected in the range from 200° C. to 260° C.

5. Process according to claim 4 wherein the step a) is carried out in a fixed or fluidized bed reactor with fluorination catalysts at a substantially constant temperature selected in the range from 220° C. to 250° C.

6. Process according to claim 1 wherein the fluorination catalysts are based on chromium oxide.

7. Process according to claim 6 wherein the used catalysts contain small amounts of iron, cobalt, aluminum, zirconium, manganese, bismuth, thorium and/or nickel oxide.

8. Process according to claim 6, wherein the used catalysts are supported on aluminum fluoride of gamma form.

9. Process according to claim 1 wherein after the step c) there is the conversion of dichlorofluoroacetylfluoride to dichlorofluoroacetylchloride (CFCl$_2$COCl) by hydrolyzing with water and then treating, at a temperature in the range −20° C.−+80° C., with thionyl chloride in a ratio of about 3/1 by moles based on the dichlorofluoroacetic acid (CFCl$_2$COOH) moles and in the presence of a 10% by moles of pyridine based on the CFCl$_2$COOH moles.

10. The process according to claim 2 wherein in step c) the separation occurs at temperatures lower than 30° C.

11. The process according to claim 2 wherein step a) is carried out in a fixed or fluidized bed reactor with fluorination catalysts at a substantially constant temperature.

* * * * *

UNITED STATES PATENT AND TRADEMARK OFFICE
CERTIFICATE OF CORRECTION

PATENT NO. : 6,166,252

DATED : December 26, 2000

INVENTOR(S) : Piero GAVEZOTTI et al.

It is certified that error appears in the above-identified patent and that said Letters Patent is hereby corrected as shown below:

```
Title page, item
[75] change ``Saronn'' to --Saronno--.
```

Signed and Sealed this

First Day of May, 2001

Attest:

NICHOLAS P. GODICI

Attesting Officer    Acting Director of the United States Patent and Trademark Office